United States Patent [19]

Sundström

[11] Patent Number: 4,472,970

[45] Date of Patent: Sep. 25, 1984

[54] METHOD OF MEASURING THE DIMENSIONS OF TOOLS AND/OR WORKPIECES OF METAL

[76] Inventor: Erik Sundström, 32 Dalkärrsleden, S-162 24 Vällingby, Sweden

[21] Appl. No.: 413,458

[22] Filed: Aug. 31, 1982

[30] Foreign Application Priority Data

Mar. 10, 1981 [SE] Sweden ................................ 8101500

[51] Int. Cl.³ ............................................. G01N 29/00
[52] U.S. Cl. ........................................ 73/584; 73/587; 73/597
[58] Field of Search .................. 73/584, 587, 596, 597, 73/658

[56] References Cited

U.S. PATENT DOCUMENTS

| | | | |
|---|---|---|---|
| 4,033,179 | 7/1977 | Romrell | 73/587 |
| 4,353,256 | 10/1982 | Moorey | 73/597 |
| 4,413,507 | 11/1983 | Drew et al. | 73/587 |

Primary Examiner—Stephen A. Kreitman
Attorney, Agent, or Firm—Burns, Doane, Swecker & Mathis

[57] ABSTRACT

The invention relates to a method of measuring the dimensions of tools and/or workpieces of metal. The measuring is characterized in that an electro-erosive material-machining discharge in a dielectric is used as transmitter of pressure waves, the time of which through the tool or workpiece to the arrival in at least three well-defined positions is scanned and gives rise to time-responsive current pulses for a digital measuring system.

5 Claims, 2 Drawing Figures

METHOD OF MEASURING THE DIMENSIONS OF TOOLS AND/OR WORKPIECES OF METAL

BACKGROUND OF THE INVENTION

This invention relates to a method of measuring tools and/or workpieces and is intended especially, but not exclusively for use at adaptive measuring with feedback of the evaluated measuring result to the tool.

The conventional measuring methods of controlling tool wear are, besides direct optical inspection, (a) detection of sound or light reflexes from tool-workpiece, which reflexes have been generated from an external source, (b) mechanic contact measuring, and (c) analysis of sound waves in workpiece or tool, which waves come from a transducer designed for this purpose.

Of these methods (a)–(c), which are feed-back methods for controlling the tool in response to wear, the methods (a) and (b) as they are developed to-day, are very sensitive to the severe environment prevailing at all cutting operations. The methods, furthermore, imply high requirements on accessibility. the costs in connection with these methods are high.

The method (c) is applied generally to crack detection, and also for determining greater distances. The use of ultrasound for measuring in metals, however, implies serious dissolution problems, due to the great sound speeds. The method (c), besides, is sensitive to interferences and has not been successfully applicable in connection with machining.

The present invention as it is defined in the attached claims renders it possible to eliminate the aforesaid disadvantages of the known measuring methods, and at the same time provides new possibilities for measuring accurately complicated tools and workpieces during the ongoing machining operation, as will become apparent from the description below.

Due to the special prerequisites applying to electro-erosive machining, spark machining, the invention has a natural field of application also here.

BRIEF DESCRIPTION OF THE DRAWING

The invention, therefore, is described in the following applied to this type of machining, with reference to the accompanying drawing, in which.

DESCRIPTION OF THE PREFERRED EMBODIMENT

Figure 1:
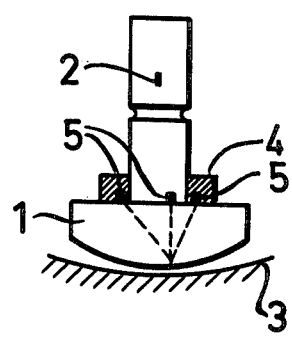
FIG. 1 shows schematically a spark machining tool.

The electrode 1 constituting the tool proper is carried in conventional manner by an electrode holder 2, which in known manner (not shown) is clamped in a machine chucking fixture. The workpiece machined by the tool is designated by 3. The details 1–3 are conventional components of electro-erosive machining tools known to-day and, therefore, are not described here in greater detail.

The machining proper by sparking, and the theories thereabout, are not a part of the present invention, either, and, therefore, it is in this case referred to as generally applied technology.

According to the invention, the measuring is carried out during the machining operation just at the moment of machining by means of the electric discharge in the dielectric medium between tool and workpiece. At the discharge an ultrasound wave is produced which, due to the relatively seen, great effect density, gives rise to great accelerations in the longitudinal direction and brings about a well-defined wave front of high speed in the electrically conductive materials, because the dielectric behaves as a Newton's liquid.

This sound wave is to be scanned, received, for example, can be realized by means of piezoelectric elements, which at the receiving emit relatively distinct signals.

In order according to the invention to measure the wear of the tool 1, three piezoelectric receivers 5 are attached by means of a ring 4 in well-defined predetermined positions fixed in relation to the tool. The arrival of the pressure wave front at the three receivers 5 in their well-defined predetermined positions, which preferably are located in one plane in common, renders it possible to unambiguously determine the spark position in the tool, because the point of time of the spark discharge is known.

Figure 2:
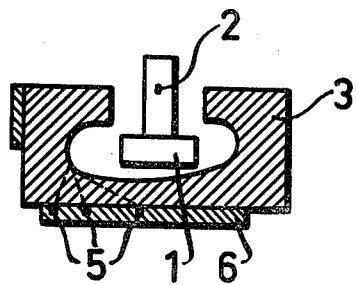
FIG. 2 shows schematically a spark machining tool and a workpiece machined by the tool.

In FIG. 2 three piezoelectric receivers are arranged in well-defined fixed positions on a plate 6, which is attached in a place suitable for measurement on the workpiece 3. The evaluation of the three signals from the receivers 5 yields an unambiguous determination of the spark position on the workpiece 3.

Due to the fact that the wave front, as mentioned, has high speed and great particle acceleration, and the piezoelectric receiver thereby emits a distinct signal, the sensitivity can be adjusted so that interferences with lower frequency are damped out, and also the contact surface of the receiver can be dimensioned small and well-defined.

The spark discharge gives rise to current pulses generated in three separate piezoelectric receivers according to this embodiment. The point of time for these three current pulses, signals, emitted in three definite places is used for evaluating and determining the position for the spark discharge. Only the point of time for the occurrence of a sound wave is used for the measuring process and, consequently, no phase shifts or other qualitative or quantitative wave parameters, which usually are applied at analog systems, are used at the measuring.

On the basis of the aforesaid, i.e. starting from the point of time of the discharge, and by using above all an external time signalling circuit, it is possible for the expert with knowledge of the computerized control technology of to-day to practically work the invention. By means of suitable evaluation and feed-back systems, spark machining equipment can be produced which during the ongoing operation continuously controls the tool for a complete compensation of the tool wear. A development thereof is a machine, which independently can carry out tool exchange and tool control for complete machining.

By the invention, the greatest disadvantages of spark machining, such as high tool costs, would be eliminated, and a more general transition to general electrodes be made possible. By using flexible electrodes it is also possible with great accuracy to machine complicated cavities "concealed" in the workpiece.

Other applications of the invention are wear research or information on optimum tool exchange criteria at manual spark machining. The invention also can be applied in other fields of engineering technology where adaptive measurement control is desired. Spark machining in a dielectricum, for example, can be introduced as a production step at line-production and in a DNC-system, informing by feed-back on the tolerance situation of cutting machines in preceding steps. Instead of spark machining as a production step, spark discharge can be introduced as a "final" step for measurement control and by feed-back to control tool exchanges in preceding machining steps.

What I claim is:

1. A method of measuring the dimensions of tools and/or workpieces of metal comprising:
    transmitting pressure waves by an electro-erosive material-machining discharge in a dielectric between the tool and the workpiece; and
    measuring pressure wave propagation time through the tool and/or workpiece and determining the position of the discharge.

2. A method as defined in claim 1 including:
    scanning a front of the pressure wave in at least three predetermined positions separated from each other on the tool and/or workpiece.

3. A method as defined in claim 1 or 2, including:
    locating the at least three predetermined positions in one plane.

4. A method as defined in claim 3, including:
    converting the pressure-wave front to time responsive current pulses for a digital measuring system by pressure-sensitive members in the at least three predetermined positions.

5. A method as defined in claim 4, including:
    forming the electro-erosive discharge from a spark formation device; and
    determining the position of the discharge for the measuring of tools and/workpieces.

* * * * *